United States Patent [19]

Hermentin et al.

[11] Patent Number: 5,260,425
[45] Date of Patent: Nov. 9, 1993

[54] ANTHRACYCLINE DERIVATIVES HAVING CYTOSTATIC ACTIVITY

[75] Inventors: Peter Hermentin, Marburg; Ernst Raab, Marburg-Dagobertshausen; Cenek Kolar; Manfred Gerken, both of Marburg; Dieter Hoffmann, Lahntal; Hans P. Kraemer, Marburg; Ulrich Stache, Hofheim am Taunus, all of Fed. Rep. of Germany

[73] Assignee: Behringwerke Aktiengesellschaft, Marburg/Lahn, Fed. Rep. of Germany

[21] Appl. No.: 360,807

[22] Filed: Jun. 2, 1989

[30] Foreign Application Priority Data

Jun. 4, 1988 [DE] Fed. Rep. of Germany ....... 3819092

[51] Int. Cl.$^5$ ............................................. C07H 15/24
[52] U.S. Cl. .................................................. 536/6.4
[58] Field of Search ............................ 536/6.4; 514/34

[56] References Cited

U.S. PATENT DOCUMENTS

| | | | |
|---|---|---|---|
| 4,591,637 | 5/1986 | Acton et al. | 536/6.4 |
| 4,888,418 | 12/1989 | Kawai et al. | 536/6.4 |
| 4,948,880 | 8/1990 | Hermentin et al. | 536/6.4 |

FOREIGN PATENT DOCUMENTS

0063776A1 11/1982 European Pat. Off.
0290744A3 11/1988 European Pat. Off.

OTHER PUBLICATIONS

Umezawa et al., "Daunomycin and Adriamycin Derivatives," Chemical Abstracts, vol. 92, No. 17, Item No. 147142f, (1980).
Acton et al., "N-(2-Hydroxyethyl)doxrubicin from Hydrolysis of 3'-Deamino-3'-(3-cyano-4-morpholinyl)doxorubicin", Journal of Medicinal Chemistry, (1986), pp. 2120-2122.
Hermentin et al., 4th European Carbohydrate Symposium, Darmstadt, FRG, Jul. 12-17, 1987.
Tong et al., J. Med. Chem., vol. 22, No. 8, 1979, pp. 912-918.

Primary Examiner—Johnnie R. Brown
Assistant Examiner—Elli Peselev
Attorney, Agent, or Firm—Finnegan, Henderson, Farabow, Garrett & Dunner

[57] ABSTRACT

The invention relates to new anthracycline derivatives having cytostatic activity and the general formula I,

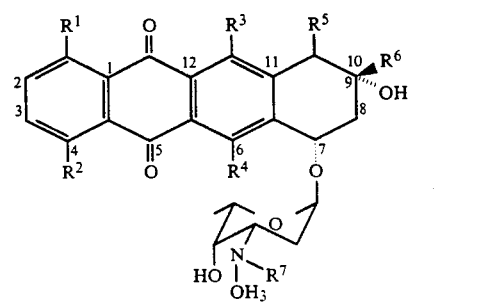

which can optionally also be in the form of an acid addition salt of physiologically acceptable inorganic or organic acids, where $R^1$ is hydrogen or a hydroxyl group, $R^2$ is hydrogen, a hydroxyl or a methoxy group, $R^3$ is hydrogen or a hydroxyl group, $R^4$ is hydrogen or a hydroxyl group, $R^5$ hydrogen, a hydroxyl or a methoxycarbonyl group, $R^6$ is $CH_2CH_3$, $COCH_3$, $COCH_2OH$, $CHOHCH_3$ or $CHOHCH_2OH$ and $R^7$ is an organic substituent which has 2 to 6 carbon atoms and which contains at least one oxygen, nitrogen or sulfur atom or a C—C double bond or a C—C triple bond, it being possible for the double bond also to be a constituent of a heteroaromatic system and for the oxygen, nitrogen or sulfur atom to be a constituent of an open-chain or heterocyclic system, to a process for the preparation thereof and to the use thereof in a pharmaceutical.

10 Claims, No Drawings

ANTHRACYCLINE DERIVATIVES HAVING CYTOSTATIC ACTIVITY

The invention relates to new anthracycline derivatives having cytostatic activity and the general formula I, to a process for the preparation thereof and to the use thereof as pharmaceuticals.

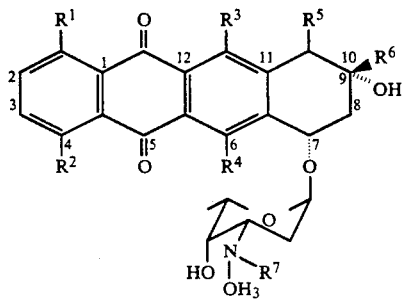

In formula I:
$R^1$ is hydrogen or a hydroxyl group,
$R^2$ is hydrogen, a hydroxyl or a methoxy group,
$R^3$ is hydrogen or a hydroxyl group,
$R^4$ is hydrogen or a hydroxyl group,
$R^5$ is hydrogen, a hydroxyl or a methoxycarbonyl group, $R^6$ is $CH_2CH_3$, $COCH_3$, $COCH_2OH$, $CHOHCH_3$ or $CHOHCH_2OH$ and $R^7$ is an organic substituent which has 2 to 6 carbon atoms and which contains at least one oxygen or nitrogen or sulfur atom or a C—C double bond or a C—C triple bond, it being possible for the double bond to be a constituent of a heteroaromatic system and for the oxygen, nitrogen or sulfur atom to be a constituent of an open-chain or heterocyclic system, excluding those compounds in which $R^7$ is a cyanomethyl group or a substituent of the general formula COR* with R*=$CH_3$, $CF_3$ or $CCl_3$.

$R^7$ is preferably

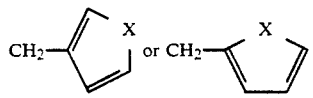

with X=O, N or S, it being possible for the heterocycle optionally to be substituted by —$CH_3$, —$NO_2$, —$CH_2OH$, —Cl or —Br, but being preferably unsubstituted.

$R^7$ is preferably a 2-picolyl(2-methylenepyridyl), 3-picolyl or 4-picolyl radical, substituted or unsubstituted, but is particularly preferably a 2-picolyl or 4-picolyl radical, $R^7$ is preferably an allyl, crotyl or propargyl, particularly preferably an allyl, radical, or $R^7$ is preferably a hydroxyalkyl having 2 to 4 carbon atoms, particularly preferably hydroxyethyl, or $R^7$ is preferably glycidyl or $R^7$ is preferably —$CH_2COOR^8$ with $R^8$=hydrogen, $C_1$-$C_4$-alkyl, branched or unbranched, substituted or unsubstituted, particularly preferably with $R^8$=hydrogen, methyl or ethyl, or $R^7$ is preferably —$CH_2CONR_2^9$ with $R^9$=hydrogen or $C_1$-$C_4$-alkyl, particularly preferably with $R^9$=hydrogen, methyl or ethyl.

The compound of the formula I can also optionally be in the form of an acid addition salt of physiologically acceptable inorganic or organic acids.

It is known that a large number of anthracyclines have cytostatic activity and that some anthracyclines such as, for example, adriamycin, daunomycin, aclacinomycin, 4'-epiadriamycin, 4'-methoxyadriamycin or 4'-deoxyadriamycin are used for the therapy of tumors.

A considerable problem in the use of these known anthracyclines for the therapy of tumors is that, besides the desired cytostatic activity, they exhibit undesired side effects such as, for example, a hematological or cardiac toxicity.

Based on this state of the art, the object of the present invention is to provide new anthracycline derivatives which, if possible, are not cross-resistant vis-a-vis adriamycin and which are distinguished by a new spectrum of action and lower toxicity compared with adriamycin and thus may advantageously be used in tumor therapy.

It has already been proposed for this purpose to mono-demethylate rhodosaminylanthracyclinones by photolytic means and to substitute or to modify selectively the resulting 3'-N-methyldaunosaminylanthracyclinones on the methylamino group thereof, resulting in very many new anthracyclines having cytostatic activity.

For example, if has already been proposed to derivatize 3'-N-methyldaunosaminylanthracyclinones in such a way that $R^7$ in formula I is cyanomethyl, COR* or $CH_2R^{10}$, where R*=H, $CH_3$, $CF_3$ or $CCl_3$ and $R^{10}$ can represent $C_1$- to $C_8$-alkyl, substituted alkyl, phenyl or substituted phenyl, it being possible for the phenyl ring to be substituted in the ortho, meta or para position by methyl, ethyl, hydroxyl, methoxy, ethoxy, nitro, cyano, fluorine, chlorine or bromine.

The anthracycline derivatives of the formula I have now been found, which are not cross-resistant vis-a-vis the anthracyclines of the state of the art in vitro and exhibit advantages with respect to their solubility in water and/or reactivity and/or toxicity. These compounds are defined by formula I.

Thus, for example, the solubility in water, which is important for the possibility of administration, of the benzyl derivatives which have already been proposed ($R^7$=benzyl or substituted benzyl) can be improved if the phenyl nucleus of the benzyl group contains a nitrogen atom, that is to say is replaced by a pyridyl radical.

Surprisingly, both the solubility in water and the cytostatic activity of a compound of the formula I is affected beneficially by comparison with the 3'-N-benzyl compound if $R^7$ is furfuryl or thenyl.

It has been found, completely surprisingly, that when $R^7$ is glycidyl the cytotoxicity of a compound of the formula I is drastically increased so that this substituent exhibits a particular advantage.

When $R^7$ is hydroxyethyl instead of ethyl or propyl, the solubility of the derivative in water is improved.

When $R^7$ is allyl the anthracycline derivative is observed to have particularly good cytostatic activity.

A process for the preparation of the new anthracycline derivatives having cytostatic activity according to the invention comprises reacting a compound of the formula I in which $R^1$=H or OH, $R^2$=H, OH or $OCH_3$, $R^3$=H or OH, $R^4$=H or OH, $R^5$=H, OH or $COOCH_3$, $R^6$=$CH_2CH_3$, $COCH_3$, $COCH_2OH$, $CHOHCH_3$ or $CHOHCH_2OH$ and $R^7$=H, either in a manner known per se (Tong et al., J. Med. Chem. (1979)

22, 912) in the presence of sodium cyanoborohydride with an aldehyde which is of 2 to 6 carbon atoms and which contains at least one oxygen, nitrogen or sulfur atom or a C—C double bond or a C—C triple bond, it being possible for the double bond also to be a constituent of a heteroaromatic system and for the oxygen, nitrogen or sulfur atom to be a constituent an open-chain or heterocyclic system, or in a manner known per se with an organohalogen compound which contains at least one oxygen, nitrogen or sulfur atom or a C—C double bond or a C—C triple bond, it being possible for the double bond also to be a constituent of a heteroaromatic system and for the oxygen, nitrogen or sulfur atom to be a constituent of an open-chain or heterocyclic system, with the proviso that halogenoacetonitrile is excepted, to give a compound of the formula I in which $R^1$ to $R^6$ have the stated meaning and $R^7$ is a substituent which contains at least one oxygen, nitrogen or sulfur atom or a C—C double bond or a C—C triple bond, it being possible for the double bond also to be a constituent of a heteroaromatic system and for the oxygen, nitrogen or sulfur atom to be a constituent of an open-chain or heterocyclic system.

The starting compounds are prepared by photolytic monodemethylation of rhodosaminylanthracyclinones in a manner known per se (Hermentin et al., 4th European Carbohydrate Symposium, Darmstadt, FRG, Jul. 12-17, 1987, Abstracts of Papers, A-144; Hermentin et al., EP 0,270,992 A2). The reaction to give the compounds of the formula I according to the invention is carried out, for example, by reaction of the relevant starting compounds of the formula I with $R^7=H$ with aldehydes or halides predetermined by the definition of $R^7$. The process conditions are known for the reaction with the aldehydes (Tong et al., J. Med. Chem. (1979) 22, 912). The reaction with halides is preferably carried out under anhydrous conditions, preferably in dimethylformamide or acetonitrile, at a temperature of 20° C. to 80° C. in the presence of a base, preferably triethylamine or potassium carbonate.

The new anthracycline derivatives obtained by the process according to the invention are distinguished by cytostatic activity and they can therefore be processed, together with the customary pharmaceutical formulating agents and/or diluents, to give pharmaceuticals for use in cancer therapy. In this connection, the mode of dosage and use essentially corresponds to that for the known substances adriamycin, daunomycin, aclacinomycin, 4'-epiadriamycin, 4'-methoxyadriamycin, or 4'-deoxyadriamycin.

The pharmaceuticals prepared in this way can, in addition, also contain other active substances as long as these do not display undesired side effects together with the compounds according to the invention.

The cytostatic activity of the compounds according to the invention has been tested using L1210 mouse leukemia cells. Employed for this purpose was the formation of colonies of L1210 leukemia cells in agar plates. This method is used to detect the effect of the test substances on the growth behavior of the cells over 1 hour or over several generations. In this connection, with a cell cycle time of 10-12 hours about 14 consecutive generations are observed in the 7 days the test lasts. In this test, the substances having cytostatic activity according to the invention bring about a reduction in the number of colonies to be observed by comparison with an untreated control sample.

Details of the test method used are evident from the descriptions hereinafter of the procedures for determining the formation of colonies.

To illustrate the preparation process according to the invention, Examples 1 to 18, in which preferred compounds according to the invention were prepared by the claimed process, are adduced hereinafter.

CHARACTERIZATION OF COMPOUNDS OF THE FORMULA I

The progress of the reactions and the resulting compounds were investigated by thin-layer chromatography or using the HPLC technique. Thin-layer chromatography was carried out on precoated silica gel plates (Merck) unless indicated otherwise. Column chromatography was carried out on silica gel 60 (Merck) of particle size 0.040-0.063 mm. The yields are not optimized.

The following solvent mixtures were used for thin-layer and column chromatography (all data in percent by volume):

| Composition | Solvent mixtures | | |
| --- | --- | --- | --- |
| | A | B | C |
| Chloroform (%) | 70 | 89 | 77 |
| Methanol (%) | 18 | 7.4 | 14 |
| Acetic acid (%) | 8.5 | 3 | 7 |
| Water (%) | 3.5 | 0.6 | 2 |

The $R_F$ values of each of the prepared compounds are compiled in Table 4.

The structures of the prepared compounds were established by $^1H$ NMR and MS spectroscopy. The $^1H$ NMR data are compiled in Table 5.

EXAMPLES

Preparation of the Starting Compounds

The starting compounds

7-O-(3'-N-methyl-alpha-L-daunosaminyl)-β-rhodamycinone A (compound of the formula I with $R^1=H$, $R^2=OH$, $R^3=R^4=R^5=OH$, $R^6=CH_2CH_3$ and $R^7=H$), 7-O-(3'-N-methyl-alpha-L-daunosaminyl)-β-isorhodomycinone B (compound of the formula I with $R^1=R^2=R^3=R^4=R^5=OH$, $R^6=CH_2CH_3$ and $R^7=H$), 7-O-(3'-N-methyl-alpha-L-daunosaminyl)-epsilonisorhodamycinone C (compound of the formula I with $R^1=R^2=R^3=R^4=OH$, $R^5=COOCH_3$, $R^6=CH_2CH_3$ and $R^7=H$), 7-O-(3'-N-methyl-alpha-L-daunosaminyl)-daunomycinone D (compound of the formula I with $R^1=H$, $R^2=OCH_3$, $R^3=R^4=OH$, $R^5=H$, $R^6=COCH_3$ and $R^7=H$), 7-O-(3'-N-methyl-alpha-L-daunosaminyl)-adriamycinone E (compound of the formula I with $R^1=H$, $R^2=OCH_3$, $R^3=R^4=OH$, $R^5=H$, $R^6=COCH_2OH$ and $R^7=H$), 7-O-(3'-N-methyl-alpha-L-daunosaminyl)-daunomycinon-13-ol F (compound of the formula I with $R^1=H$, $R^2=OCH_3$, $R^3=R^4=OH$, $R^5=H$, $R^6=CHOHCH_3$ and $R^7=H$) and 7-O-(3'-N-methyl-alpha-L-daunosaminyl)-4-O-methyl-β-rhodomycinone G (compound of the formula I with $R^1=H$, $R^2=OCH_3$, $R^3=R^4=OH$, $R^5=OH$, $R^6=CH_2CH_3$ and $R^7=H$) were prepared in a manner known per se (Hermentin et al., 4th European Carbohydrate Symposium, Darmstadt, FRG, Jul. 12–17, 1987, Abstracts of Papers, A-144; Hermentin et al., EP 0,270,992 A2) by photolytic demethylation of the corresponding 7-O-alpha-L-rhodosaminylanthracyclinones:

A was prepared from β-rhodomycin I (7-O-alpha-L-rhodosaminyl-β-rhodomycinone);
B was prepared from β-isorhodomycin I (7-O-alpha-L-rhodosaminyl-β-isorhodomycinone);
C was prepared from 7-O-alpha-L-rhodosaminyl-epsilon-isorhodomycinone;
D was prepared from N,N-dimethyldaunomycin (7-O-alpha-L-rhodosaminyldaunomycinone);
E was prepared from N,N-dimethyladriamycin (7-O-alpha-L-rhodosaminyladriamycinone);
F was prepared from N,N-dimethyldaunomycin-13-ol (7-O-alpha-L-rhodosaminyldaunomycinon-13-ol);
G was prepared from 4-O-methyl-β-rhodomycin I (4-O-methyl-7-O-alpha-L-rhodosaminyl-β-rhodomycinone).

EXAMPLE 1

7-O-(3'-N-Allyl-3'-N-methyl-alpha-L-daunosaminyl)-β-rhodomycinone (compound 1)

75 μl (105 mg=0.867 mmol=1.53 equiv.) of allyl bromide were added to a solution of 7-O-(3'-N-methylalpha-L-daunosaminyl)-β-rhodomycinone (300 mg=0.567 mmol) and triethylamine (240 μl=174 mg=1.72 mmol=3.0 equiv.) in 30 ml of dry dimethylformamide, and the mixture was stirred at room temperature in the dark. After 16 h further triethylamine (80 μl=58 mg 0.574 mmol=1.0 equiv.) and allyl bromide (25 μl=35 mg=0.289 mmol=0.51 equiv.) were added, and the mixture was stirred for a further 16 h. It was then evaporated to dryness in a rotary evaporator under high vacuum, and the reaction mixture was subjected to two column chromatographies on silica gel (30 g and 20 g respectively) in solvent mixture C ($R_F$ 0.49). Water was added to the combined fractions for phase separation, the pH was brought to 7 with 10% (w/v) sodium hydroxide solution and then the pH was adjusted to 8 by addition of saturated aqueous sodium bicarbonate solution. The phases were then separated in a separating funnel, the aqueous phase was extracted several times with chloroform, and the combined organic phases were evaporated to dryness in a rotary evaporator.

Yield: 153 mg (0.27 mmol)=47%

EXAMPLE 2

7-O-(3'-N-methyl-3'-N-proparayl-alpha-L-daunosaminyl)-β-rhodomycinone (compound 2)

53 mg (0.10 mmol) of 7-O-(3'-N-methyl-alpha-L-daunosaminyl)-β-rhodomycinone and 106 μl of 80% strength propargyl bromide in toluene (113 mg=0.95 mmol 9.5 equiv.) were reacted in the presence of 40 μl (29 mg=0.287 mmol=2.87 equiv.) of triethylamine in analogy to Example 1 for 30 min and chromatographed on 10 g of silica gel in solvent mixture B ($R_F$0.29) and worked up.

Yield: 31 mg (0.055 mmol)=55%
MS-FAB (M+H$^+$) m/e=568

EXAMPLE 3

7-O-(3'-N-Hydroxyethyl-3'-N-methyl-alpha-L-daunosaminyl)-β-rhodomycinone (compound 3)

30 mg (0.057 mmol) of 7-O-(3'-N-methyl-alpha-L-daunosaminyl)-β-rhodomycinone and 50 μl (88 mg=0.71 mmol 12.4 equiv.) of bromoethanol were reacted in the presence of 24 μl (17 mg=0.17 mmol=3.0 equiv.) of triethylamine in analogy to Example 1 for 4 days and were worked up. For the column separation 15 g of silica gel were equilibrated with a chloroform/ethanol mixture (20/1). The liquid product mixture was then loaded on the column, and the excess bromoethanol and dimethylformamide contained therein was washed out with chloroform/methanol (20/1) (about 150 ml). The reaction product which remained at the loading point was subsequently chromatographed in solvent mixture A ($R_F$ 0.58) and worked up in analogy to Example 1.

Yield: 14 mg (0.024 mmol)=42%

EXAMPLE 4

7-O-(3'-N-Methyl-3'-N-(4-picolyl)-alpha-L-daunosaminyl)-β-rhodomycinone (compound 4)

50 μl (53 mg=0.88 mmol=4.7 equiv.) of acetic acid and 800 mg (713 μl=7.47 mmol=39.5 equiv.) of pyridine-4-aldehyde were added to a solution of 100 mg (0.189 mmol) of 7-O-(3'-N-methyl-alpha-L-daunosaminyl)-β-rhodomycinone in 10 ml of acetonitrile/water (4/1), and the mixture was stirred at room temperature in the dark for 2 h. Then sodium cyanoborohydride (240 mg=3.82 mmol=20 equiv.) was added, and the reaction was stirred for a further 2 h. The reaction solution was then poured into an aqueous sodium bicarbonate solution and extracted with chloroform. The combined chloroform phases were extracted anew with water of pH 13 (addition of sodium hydroxide solution), during which the excess pyridyl compound remained in the chloroform and the anthracycline (as sodium salt; blue coloration) remained in the water. The aqueous phase was adjusted to pH 8 and then the anthracycline was extracted with chloroform and chromatographed on 12 g of silica gel in solvent mixture B ($R_F$ 0.23) and worked up in analogy to Example 1.

Yield: 42 mg (0.068 mmol)=36%

EXAMPLE 5

7-O-(3'-N-Methyl-3'-N-(2-picolyl)-alpha-L-daunosaminyl)-β-rhodomycinone (compound 5)

20 mg (0.038 mmol) of 7-O-(3'-N-methyl-alpha-L-daunosaminyl)-β-rhodomycinone and 160 mg (142 μl=1.49 mmol=39 equiv.) of pyridine-2-aldehyde were reacted in analogy to Example 4; the column chromatography was carried out in solvent mixture C ($R_F$ 0.79).

Yield: 14 mg (0.023 mmol)=60%

EXAMPLE 6

7-O-(3'-N-(2-Furfuryl)-3'-N-methyl-alpha-L-daunosaminyl)-β-rhodomycinone (compound 6)

200 mg (0.38 mmol) of 7-O-(3'-N-methyl-alpha-L-daunosaminyl)-β-rhodomycinone and 1.5 ml (1734 mg=18.0 mmol=47 equiv.) of furfural were reacted in analogy to Example 4, with stirring being continued for 40 h after the addition of sodium cyanoborohydride.

The solution was then poured into water, the pH was adjusted to 8 with sodium bicarbonate, the mixture was extracted with chloroform, and the solvent was removed in a rotary evaporator. The resulting product mixture was dried under high vacuum to remove excess furanyl compound and then chromatographed on 20 g of silica gel in solvent mixture C ($R_F$ 0.57) and rechromatographed in solvent mixture B ($R_F$ 0.22).

Yield: 129 mg (0.21 mmol) = 55%

EXAMPLE 7

7-O-(3'-N-Acetamido-3'-N-methyl-alpha-L-daunosaminyl)-β-rhodomycinone (compound 7)

30 mg (0.057 mmol) of 7-O-(3'-N-methyl-alpha-L-daunosaminyl)-β-rhodomycinone and 30 mg (0.162 mmol = 2.84 equiv.) of iodoacetamide were reacted in the presence of 24 μl (17.4 mg = 0.17 mmol = 3.0 equiv.) of triethylamine for 16 h in analogy to Example 1, but using acetonitrile (6 ml) as solvent. The product mixture was chromatographed on 6 g of silica gel in solvent mixture C ($R_F$ 0.31) and worked up in analogy to Example 1.

Yield: 19 mg (0.032 mmol) = 56%

EXAMPLE 8

7-O-(3'-N-Glycidyl-3'-N-methyl-alpha-L-daunosaminyl)-β-rhodomycinone (compounds 8m, 8a and 8b)

A mixture of 7-O-(3'-N-methyl-alpha-L-daunosaminyl)-β-rhodomycinone (200 mg = 0.378 mmol), epibromohydrin (400 μl = 640 mg = 4.675 mmol = 12.4 equiv.) and potassium carbonate (400 mg) in dry acetonitrile (25 ml) was stirred at 60° C. in the dark for 30 h. It was then concentrated in a rotary evaporator, the residue was taken up in chloroform/ethanol (20/1), and the solution was filtered and chromatographed on 20 g of silica gel in chloroform/ethanol (20/1). Isolated from this was, according to $^1$H NMR, a 1:1 mixture of isomers (compound 8 m) in a yield of 102 mg (0.17 mmol = 45%). Rechromatography in chloroform/ethanol (20/1) allowed the mixture of isomers 8m to be partially separated into the pure isomers 8a ($R_F$ 0.35) and 8b ($R_F$ 0.32).

MS-FAB (M+H$^-$) m/e = 586

EXAMPLE 9

7-O-(3'-N-Allyl-3'-N-methyl-alpha-L-daunosaminyl)-β-isorhodomycinone (compound 9)

300 mg (0.55 mmol) of 7-O-(3'-N-methyl-alpha-L-daunosaminyl)-β-isorhodomycinone and 100 μl (140 mg = 1.16 mmol = 21 equiv.) of allyl bromide were reacted in the presence of 330 μl (240 mg = 2.4 mmol = 44 equiv. ) of triethylamine in analogy to Example 1. After 16 h a further 165 μl (2.2 equiv.) of triethylamine and 50 μl (1 equiv.) of allyl bromide were added, and the mixture was stirred at room temperature in the dark for a further 6 h. It was then evaporated to dryness under high vacuum, and the product mixture was chromatographed on 52 g of silica gel in solvent C ($R_F$ 0.52). The collected fractions were worked up in analogy to Example 1.

Yield: 154 mg (0.26 mmol) = 48%

EXAMPLE 10

7-O-(3'-N-(Ethoxycarbonylmethyl)-3'-N-methyl-alpha-L-daunosaminyl)-β-rhodomycinone (compound 10)

100 mg (0.189 mmol) of 7-O-(3'-N-methyl-alpha-L-daunosaminyl)-β-rhodomycinone and 75 μl (113 mg = 0.677 mmol = 3.58 equiv.) of ethyl bromoacetate were reacted in the presence of 80 μl (58 mg = 0.574 mmol = 3.0 equiv.) of triethylamine in analogy to Example 1 for 2 h. The product mixture was dissolved in a little chloroform without delay after evaporation, and was loaded on a silica gel column (15 g of silica gel) made up in ether and eluted with about 100 ml of ether to remove the excess bromoacetate. Compound 10 was subsequently eluted in chloroform/ethanol (20/1) ($R_F$ 0.32).

Yield: 70 mg (0.114 mmol) = 60%

EXAMPLE 11

7-O-(3'-N-Carboxymethyl-3'-N-methyl-alpha-L-daunosaminyl)-β-rhodomycinone (compound 11)

20 mg (0.038 mmol) of 7-O-(3'-N-methyl-alpha-L-daunosaminyl)-β-rhodomycinone and 15 μl (29 mg = 0.21 mmol = 5.5 equiv.) of bromoacetic acid were reacted in the presence of 16 μl (11.6 mg = 0.115 mmol = 3.0 equiv.) of triethylamine in analogy to Example 1 for 2 h, and the $R_F$ was determined.

EXAMPLE 12

7-O-(3'-N-Methyl-3'-N-(3-thenyl)-alpha-L-daunosaminyl)-β-rhodomycinone (compound 12)

20 mg (0.038 mmol) of 7-O-(3'-N-methyl-alpha-L-daunosaminyl)-β-rhodomycinone and 156 μl (200 mg = 0.178 mmol = 47 equiv.) of thiophene-3-aldehyde were reacted in analogy to Example 4 and, after addition of sodium cyanoborohydride (48 mg = 0.76 mmol = 20 equiv.), the mixture was stirred at room temperature for a further 16 h. Column chromatography was carried out first in chloroform (to remove excess thiophene compound) and then in solvent mixture B ($R_F$ 0.22).

Yield: 9.2 mg (0.015 mmol) = 39%

EXAMPLE 13

7-O-(3'-N-Methyl-3'-N-(2-thenyl)-alpha-L-daunosaminyl)-β-rhodomycinone (compound 13)

20 mg (0.038 mmol) of 7-O-(3'-N-methyl-alpha-L-daunosaminyl)-β-rhodomycinone and 167 μl (200 mg = 0.178 mmol = 47 equiv.) of thiophene-2-aldehyde were reacted in analogy to Example 4 and, after addition of sodium cyanoborohydride (48 mg = 0.76 mmol = 20 equiv.), the mixture was stirred first at room temperature for 16 h and then at 50° C. for a further 8 h. The column chromatography was carried out on 4 g of silica gel in solvent mixture B ($R_F$ 0.25); rechromatography was then carried out on 3 g of silica gel in solvent mixture C ($R_F$ 0.63).

Yield: 8.2 mg (0.013 mmol) = 34%

EXAMPLE 14

7-O-(3'-N-Glycidyl-3'-N-methyl-alpha-L-daunosaminyl)-β-isorhodomycinone (compound 14m)

A mixture of 7-O-(3'-N-methyl-alpha-L-daunosaminyl)-β-isorhodomycinone (85 mg = 0.156 mmol), epibromohydrin (125 μl = 185 mg = 1.35 mmol = 8.7 equiv.) and potassium carbonate (125 mg) in dry dimethylformamide (8 ml) was stirred at 70° C. in the dark for 3 h. It was then concentrated in a rotary evaporator and dried under high vacuum overnight. The residue was dissolved in water, and the pH was adjusted to 7.0 with dilute hydrochloric acid. The product was extracted by shaking with chloroform and chromatographed on 12 g of silica gel in a mixture of solvent B and solvent C (1/1), and the collected fractions were worked up in analogy to Example 1.

Yield: 68 mg (0.11 mmol) = 70%

EXAMPLE 15

7-O-(3'-N-Allyl-3'-N-methyl-alpha-L-daunosaminyl)-daunomycinone (compound 15)

30 mg (0.055 mmol) of 3'-N-methyldaunomycin and 10 μl (14 mg = 0.116 mmol = 2.1 equiv.) of allyl bromide were reacted in the presence of 33 μl (24 mg = 0.24 mmol 4.4 equiv.) of triethylamine for 24 h, and the working up was carried out, in analogy to Example 1, and chromatography was carried out in solvent C ($R_F$ 0.53) on 5 g of silica gel. The collected fractions were worked up in analogy to Example 1.

Yield: 17 mg (0.029 mmol) = 53%

EXAMPLE 16

7-O-N-Allyl-3'-N-methyl-alpha-L-daunosaminyl)-adriamycinone (compound 16)

32 mg (0.057 mmol) of 3'-N-methyladriamycin and 10 μl (14 mg = 0.116 mmol = 2.0 equiv.) of allyl bromide were reacted in the presence of 33 μl (24 mg = 0.24 mmol = 4.2 equiv.) of triethylamine for 24 h, and the working up was carried out, in analogy to Example 1, and chromatography was carried out in solvent C ($R_F$ 0.22) on 5 g of silica gel. The collected fractions were worked up in analogy to Example 1.

Yield: 14 mg (0.023 mmol) = 40%

EXAMPLE 17

7-O-(3'-N-Allyl-3'-N-methyl-alpha-L-daunosaminyl)-4-O-methyl-β-rhodomycinone (compound 17)

29 mg (0.053 mmol) of 7-O-(3'-N-methyl-alpha-L-daunosaminyl)-4-O-methyl-β-rhodomycinone and 10 μl (14 mg = 0.116 mmol = 2.2 equiv.) of allyl bromide were reacted in the presence of 33 μl (24 mg = 0.24 mmol = 4.5 equiv.) of triethylamine for 24 h, and working up was carried out, in analogy to Example 1, and chromatography was carried out in a mixture of solvent B and solvent C (1/1) on 5 g of silica gel. The collected fractions were worked up in analogy to Example 1.

Yield: 18 mg (0.031 mmol) = 58%

EXAMPLE 18

7-O-(3'-N-Acetonyl-3'-N-methyl-alpha-L-daunosaminyl)-β-rhodomycinone (compound 18)

53 mg (0.10 mmol) of 7-O-(3'-N-methyl-alpha-L-daunosaminyl)-β-rhodomycinone and 0.5 ml (580 mg = 6.27 mmol) of chloroacetone were stirred in the presence of 1 g of potassium carbonate in 10 ml of dimethylformamide in the dark for 16 h. The solution was then filtered and concentrated and extracted by shaking with chloroform/water under neutral conditions. The product in the organic phase was chromatographed on 10 g of silica gel in solvent B ($R_F$ 0.16). The collected fractions were worked up in analogy to Example 1.

Yield: 27 mg (0.046 mmol) = 46%

CYTOTOXICITY OF COMPOUNDS OF THE FORMULA I ON L1210 MOUSE LEUKEMIA CELLS IN VITRO

Procedure for determining the formation of colonies of L1210 leukemia cells in soft agar 500 leukemia cells per plate were incubated with various concentrations of the test substance at 37° C. for 1 hour. The cells were then washed twice with McCoy5A medium and finally, after addition of 0.3% agar, poured into Petri dishes. Controls were incubated only with fresh medium. In place of the incubation for one hour, in some cases various concentrations and test substances were mixed with the upper agar layer in order in this way to achieve continuous exposure of the cells throughout the incubation time. After the agar had solidified, the plates were incubated in an incubator at 37° C. for 7 days (5% by volume $CO_2$, 95% relative humidity). The number of colonies which had been produced with a diameter of more than 60 μm was then counted. The results have been reported as the number of colonies in treated agar plates as a percentage of the untreated control. The $IC_{50}$ was determined as a measure of the activity of the substance from the dose-effect plot obtained in this way. The results for the compounds described herein, by comparison with adriamycin, are compiled in Table 1.

TABLE 1a[1)]

| Substance No. (Example) | Prepared compounds of the formula I | | | | |
|---|---|---|---|---|---|
| | $R^1$ | $R^2$ | $R^5$ | $R^6$ | $R^7$ |
| Adriamycin | | | (Reference) | | |
| 1 | H | OH | OH | $CH_2CH_3$ | $CH_2CHCH_2$ |
| 2 | H | OH | OH | $CH_2CH_3$ | $CH_2CCH$ |
| 3 | H | OH | OH | $CH_2CH_3$ | $CH_2CH_2OH$ |
| 4 | H | OH | OH | $CH_2CH_3$ | 4-picolyl |
| 5 | H | OH | OH | $CH_2CH_3$ | 2-picolyl |
| 6 | H | OH | OH | $CH_2CH_3$ | furfuryl |
| 7 | H | OH | OH | $CH_2CH_3$ | $CH_2CONH_2$ |
| 8m[2)] | H | OH | OH | $CH_2CH_3$ | glycidyl |
| 8a[3)] | H | OH | OH | $CH_2CH_3$ | glycidyl-a |
| 8b[3)] | H | OH | OH | $CH_2CH_3$ | glycidyl-b |
| 9 | OH | OH | OH | $CH_2CH_3$ | $CH_2CHCH_2$ |
| 10 | H | OH | OH | $CH_2CH_3$ | $CH_2COOCH_2CH_3$ |
| 11 | H | OH | OH | $CH_2CH_3$ | $CH_2COOH$ |
| 12 | H | OH | OH | $CH_2CH_3$ | 3-thenyl |
| 13 | H | OH | OH | $CH_2CH_3$ | 2-thenyl |
| 14m[2)] | OH | OH | OH | $CH_2CH_3$ | glycidyl |
| 15 | H | $OCH_3$ | H | $COCH_3$ | $CH_2CHCH_2$ |
| 16 | H | $OCH_3$ | H | $COCH_2OH$ | $CH_2CHCH_2$ |
| 17 | H | $OCH_3$ | OH | $CH_2CH_3$ | $CH_2CHCH_2$ |
| 18 | H | OH | OH | $CH_2CH_3$ | $CH_2COCH_3$ |

[1)] for the said compounds. $R^3 = R^4 = OH$
[2)] m: mixture of the two isomers a and b
[3)] a and b: pure isomers without assignment of structures TABLE 1b

| Cytotoxicity of the prepared compounds of the formula I on L1210 leukemia cells in vitro | | |
|---|---|---|
| Substance No. (Example) | Continuous incubation $IC_{50}$(μg/ml) | 1 h incubation $IC_{50}$(μg/ml) |
| Adriamycin | 0.02 | 0.04 |
| 1 | 0.01 | 0.08 |
| 2 | 0.08 | 0.3 |
| 3 | 0.02 | 0.044 |
| 4 | 0.023 | 0.1 |
| 5 | 0.038 | 0.24 |

TABLE 1b-continued
Cytotoxicity of the prepared compounds of the formula I on L1210 leukemia cells in vitro

| Substance No. (Example) | Continuous incubation IC$_{50}$(μg/ml) | 1 h incubation IC$_{50}$(μg/ml) |
|---|---|---|
| 6 | 0.03 | 0.038 |
| 7 | 0.084 | 0.24 |
| 8m[1] | 0.002 | 0.0072 |
| 8a[2] | 0.001 | 0.0034 |
| 8b[2] | 0.003 | 0.01 |
| 9 | 0.008 | 0.5 |
| 10 | 0.1 | 0.06 |
| 11 | — | — |
| 12 | 0.032 | 0.17 |
| 13 | 0.034 | 0.38 |
| 14m[1] | 0.005 | 0.0024 |
| 15 | 0.008 | above 1 |
| 16 | — | — |
| 17 | 0.036 | above 1 |
| 18 | 0.018 | 0.073 |

[1] m: mixture of the two isomers a and b
[2] a and b: pure isomers without assignment of structures

DETERMINATION OF THE CROSS-RESISTANCES IN VITRO BY COMPARISON WITH ADRIAMYCIN

PROLIFERATION TEST (MTT REDUCTION)

L1210, A 549 or HT 29 in the exponential phase of growth are incubated in a cell density of $5 \times 10^3$ cells/ml in RPMI 1640 in a 96-well microtiter plate with various concentrations of the test substance at 37° C., 5% $CO_2$ and 95% relative humidity for 72 h. Control experiments receive merely growth medium in place of the test substance. Quadruplicate determinations are set up for each test substance and for the control. After incubation for 65 h, 50 μl of an MTT solution (2.5 mg/ml; MTT=3-(4,5-dimethylthiazol-2-yl)-2,5-diphenyltetrazoliumbromide) in phosphate-buffered saline) are added. MTT is reduced to a dark red insoluble formazan dyestuff in the presence of live cells. This reaction is complete after 7 h (L1210 cells) or after 24 h (A 549, HT 29 cells), and the supernatant medium is carefully removed by aspiration. The insoluble dyestuff is dissolved by addition of 100 μl of DMSO (dimethyl sulfoxide) and the extinction of the resulting solution at a wavelength of 492 nm is then measured for each well in a multiscan 340 CC photometer from Flow.

The ratio of the extinctions for treated and untreated cells provides a dose-effect plot from which the concentration which just kills 50% of the cells (IC$_{50}$) can be read off. The coefficient of variation for repeat investigations is less than 15%.

The cross-resistance between the particular test compound and doxorubicin as standard compound is determined with the aid of the MTT test (see above for method) on sensitive and resistant L1210 leukemia cells.

The resistant cell line was established by incubation of a sensitive subline with the reference compound in concentrations which increased stepwise.

The IC$_{50}$ of the test compound on the resistant subline related to the IC$_{50}$ of the sensitive subline provides both the degree of resistance for the test Compound (DR$_{(T)}$) and that for the reference compound (DR$_{(R)}$) in accordance with the formula $$DR_{T,R} = \frac{IC_{50} \text{ resistant cell line}}{IC_{50} \text{ sensitive cell line}}$$

In addition, the degree of cross-resistance (DCR) for the test compound is calculated in accordance with the formula $$DCR \% = \frac{DR_{(T)} - 1}{DR_{(R)}} \times 100$$

In the case where the loss of effect of the test compound on the resistant line in relation to the sensitive line is greater than that of the reference compound it is possible for the degree of cross-resistance to be above 100%.

The results compiled in Table 2 show that substances 1, 4 and 6 which have been investigated hitherto are not cross-resistant to doxorubicin.

TABLE 2

| Substance No. | Test system | Incubation time | Degree of resistance of the cell | Cross-resistance to adriamycin |
|---|---|---|---|---|
| Adriamycin | MTT | 3d | 60–80 | 100.0 |
| 1 | MTT | 3d | 10.0 | 19.0 |
| 4 | MTT | 3d | 1.6 | 0.2 |
| 6 | MTT | 3d | 2.0 | 2.0 |

IN VIVO DATA OF THE PREPARED COMPOUNDS

Determination of the Indicative Toxicity

To determine the indicative toxicity, NMRI mice receive an intraperitoneal injection of various doses of the test substance dissolved in 0.5 ml of 5% strength glucose solution on day 0. Control groups receive merely 0.5 ml of 5% strength glucose solution. 5 mice are used for each concentration of the test substance. The number of mice surviving on day 14 is determined, and from this the LD5, LD50 and LD95 are determined by the Litchfield-Wilcoxon method. The toxicity (LD50 (mg/kg)) of the compounds described here is summarized in Table 3 by comparison with adriamycin.

In vivo activity of compounds of the formula I on L1210 leukemia of the mouse

Method

Ascites fluid is removed from DBA2 mice (female, 18–20 g) under sterile conditions 7 days after inoculation of tumor cells. The ascites is washed three times with PBS (phosphate-buffered saline), counted and adjusted to a cell count of $10^6$ in 0.2 ml of PBS.

$10^6$ cells, suspended in 0.2 ml of PBS, are then injected intraperitoneally into DBF1 mice (female, 18–20 g). 6 animals per group are used for each substance concentration and as controls.

Determination of the Antitumor Activity a) The animals are weighed on days 1 and 5 after injection of the test substance. A weight loss of more than 20% on day 5 is regarded as an indicator of a toxic effect of the substance.
b) At the end of the experiment (death of all animals or surviving animals on day 60) the mean survival time of the animals in the particular groups is determined as long as at least 65% of the animals were still alive on day 5 of the experiment. The mean survival time is determined only for animals which die during the course of the experiment. Long-term survivors (LTS) are not included in this calculation and are reported separately.

The antitumor activity (T/C) for the particular substance concentration is determined from the mean survival time ($MST_T$) in the treated groups and in the control groups ($MST_C$) as a percentage of the untreated controls in accordance with the following formula:

$$T/C = \frac{MST_T}{MST_c} \times 100$$

The T/C values and the treatment regimen employed in each case are compiled in Table 3, together with the indicative toxicity. T/C values greater than 125% are regarded as an indicator of a significant antitumor activity of the test substance.

TABLE 3

Effect of the prepared compounds in vivo

| Substance No. (Example) | Indicative toxicity LD$_{50}$(mg/kg) | | L1210-Leukemia in vivo T/C[3]/dose (mg/kg) | |
|---|---|---|---|---|
| | 3xip,q3d[1] | 3xiv,q3d[2] | 3xip,q3d[1] | 3xiv,q3d[2] |
| 1 | 1-5 | | 200/1.19 | 146/1.00 |
| 2 | | 2-5 | | 144/1.20 |
| 3 | 0.2-1 | | | 108/1.13 |
| 4 | 2.5-5 | | | |
| 6 | 1-5 | | 141/2.80 | 129/2.80 |
| 7 | 2-5 | | | 142/11.2 |
| 8m | 0.75-1.5 | | 114/0.47 | |
| 9 | above 6 | | | |
| 10 | 10-25 | | | 132/12.7 |
| 12 | | 2-5 | | |
| 14 | | 0.3-0.75 | | 104/0.13 |

TABLE 3-continued

Effect of the prepared compounds in vivo

| Substance No. (Example) | Indicative toxicity LD$_{50}$(mg/kg) | | L1210-Leukemia in vivo T/C[3]/dose (mg/kg) | |
|---|---|---|---|---|
| | 3xip,q3d[1] | 3xiv,q3d[2] | 3xip,q3d[1] | 3xiv,q3d[2] |
| Adriamycin | 2.7 | | 154[4] | |

[1] 3xip,q3d: three intraperitoneal administrations with an interval of 3 days between each
[2] 3xiv,q3d: three intravenous administrations with an interval of 3 days between each
[3] T/C: survival rate expressed as a % of the control
[4] Two of 6 animals recovered (long-term survivors)

TABLE 4

$R_F$ values of the prepared compounds

| Substance No. (Example) | Solvent mixture | | | Chloroform/ethanol (20/1) |
|---|---|---|---|---|
| | A | B | C | |
| 1 | 0.77 | 0.18 | 0.49 | 0.27 |
| 2 | 0.82 | 0.29 | 0.56 | 0.45 |
| 3 | 0.58 | 0.054 | 0.28 | 0.03 |
| 4 | 0.63 | 0.23 | 0.47 | 0.21 |
| 5 | 0.90 | 0.38 | 0.79 | — |
| 6 | 0.76 | 0.22 | 0.57 | 0.26 |
| 7 | 0.58 | 0.11 | 0.31 | 0.13 |
| 8a | 0.72 | 0.17 | 0.44 | 0.35 |
| 8b | 0.72 | 0.17 | 0.44 | 0.32 |
| 9 | 0.78 | 0.17 | 0.52 | 0.24 |
| 10 | 0.88 | 0.42 | 0.74 | 0.32 |
| 11 | 0.50 | 0.05 | 0.32 | 0 |
| 12 | 0.78 | 0.22 | 0.59 | 0.25 |
| 13 | 0.82 | 0.25 | 0.63 | 0.35 |
| 14a | 0.73 | 0.11 | 0.45 | 0.32 |
| 14b | 0.73 | 0.11 | 0.45 | 0.28 |
| 15 | 0.62 | 0.16 | 0.53 | 0.24 |
| 16 | 0.31 | 0.012 | 0.22 | 0.014 |
| 17 | 0.62 | 0.12 | 0.53 | 0.19 |
| 18 | 0.69 | 0.16 | 0.58 | 0.27 |

TABLE 5

300 MHz $^1$H NMR data of various compounds of the formula I

The substance numbers in the first line correspond to the revelant Example numbers. The spectra were recorded in CDCl$_3$ with tetramethylsilane as internal standard, unless noted otherwise.

Abbreviations:
- s = singlet
- d = doublet
- t = triplet
- q = quartet
- dd = doublet of doublets
- ddd = doublet of doublet of doublets
- dt = doublet of triplets
- dq = doublet of quartets
- bs = broad singlet

| Substance No. (Proton) | 1 | | | 2 | | 3 | | 4 | | |
|---|---|---|---|---|---|---|---|---|---|---|
| | a | b | c | a | b | a | b | a | b | c |
| | $R^7$: CH$_2$CHCH$_2$ | | | CH$_2$CCH | | CH$_2$CH$_2$OH | | CH$_2$—C$_6$H$_5$N | | |
| H-1 | 7.89dd | | | 7.88d | | 7.88dd | | 7.90dd | | |
| H-2 | 7.72t | | | 7.72t | | 7.72t | | 7.73t | | |
| H-3 | 7.33dd | | | 7.33dd | | 7.33dd | | 7.34dd | | |
| H-7 | 5.15m | | | 5.15m | | 5.15m | | 5.17m | | |
| H-8alpha | 2.12dd | | | 2.12dd | | 2.12dd | | 2.12dd | | |
| H-8β | 2.26d | | | 2.26d | | 2.24d | | 2.27d | | |
| H-10 | 4.91s | | | 4.91s | | 4.91s | | 4.93s | | |
| H$_2$-13 | 1.7-1.9m | | | 1.7-1.9m | | 1.7-1.9m | | 1.7-1.9m | | |
| H$_3$-14 | 1.12t | | | 1.12t | | 1.12t | | 1.13t | | |
| H-1' | 5.51bs | | | 5.52d | | 5.52bs | | 5.55bs | | |
| H$_2$-2' | 1.7-1.9m | | | 1.7-1.9m | | 1.7-1.9m | | 1.17-1.9m | | |
| H-3' | 2.48dt | | | 2.64ddd | | 2.5-2.7m | | 2.62dt | | |
| H-4' | 3.70bs | | | 3.69d | | 3.76bs | | 3.80bs | | |
| H-5' | 4.08q | | | 4.09q | | 4.12q | | 4.14q | | |
| H$_3$-6' | 1.41d | | | 1.41d | | 1.38d | | 1.43d | | |

TABLE 5-continued

300 MHz $^1$H NMR data of various compounds of the formula I

| | | | | |
|---|---|---|---|---|
| N—CH$_3$ | 2.18s | 2.31s | 2.26s | 2.12s |
| OH-4 | 12.15bs | | | 12.14bs |
| OH-6 | 12.84bs | | | 12.86bs |
| OH-11 | 12.84bs | | | 12.86bs |
| OH-11 | 13.63bs | | | 13.63bs |
| a | 2.97dd, | 3.39dd, | 2.5–2.75m | 3.45d |
| | 3.15dd; | 3.41dd; | | 3.62d; |
| | $J_{aa'}=14Hz$ | $J_{aa'}=18Hz$ | | $J_{aa'}=14Hz$ |
| | $J_{ab}=J_{a'b}=7Hz$ | $J_{ab}=J_{a'b}=2Hz$ | | |
| b | 5.6–5.8m | 2.12t; | 3.61t; | 7.17d; |
| | | $J_{ab}=J_{a'b}=2Hz$ | $J=5Hz$ | $J_{bc}=6Hz$ |
| c | 5.05–5.15m | | | 8.51d; |
| | | | | $J_{bc}=6Hz$ |

| | 5 | 6 | 7[1)] |
|---|---|---|---|
| Substance No. (Proton) | R$_7$: CH$_2$— (pyridine ring a,b,c,d,e,N) | CH$_2$— (furan ring a,b,c,d,O) | a b CH$_2$CONH$_2$ |
| H-1 | 7.89d | 7.89d | 7.86d |
| H-2 | 7.72t | 7.72t | 7.72t |
| H-3 | 7.33d | 7.33d | 7.31d |
| H-7 | 5.17m | 5.16m | 5.12bs |
| H-8alpha | 2.12dd | 2.12dd | |
| H-8β | 2.28d | 2.26d | 2.19bs |
| H-10 | 4.93s | 4.91s | 4.83s |
| H$_2$-13 | 1.7–2.0m | 1.7–2.0m | 1.7–1.9m |
| H$_3$-14 | 1.13t | 1.12t | 1.10t |
| H-1' | 5.55bs | 5.53bs | 5.49bd |
| H-2' | 1.7–2.0m | 1.7–1.95m | 1.97dt[2)]; 1.7–1.9m |
| H-3' | 2.62dt | 2.5–2.7m | 3) |
| H-4' | 3.83bs | 3.81bs | 3.72bs |
| H-5' | 4.15q | 4.10q | 4.07q |
| H$_3$-6' | 1.43d | 1.42d | 1.34d |
| N—CH$_3$ | 2.22s | 2.22s | 2.30s |
| OH-4 | 12.16bs | 12.15bs | |
| OH-6 | 12.84bs | 12.85bs | |
| OH-11 | 13.61bs | 12.63bs | |
| a | 3.59d,3.81d; | 3.59d,3.72d; | 3.02d,3.09d; |
| | $J_{aa'}=14Hz$ | $J_{aa'}=15Hz$ | $J_{aa'}=8.5Hz$ |
| b | 7.24d; $J_{bc}=8Hz$ | 6.12d; $J_{bc}=3Hz$ | 5.97bs(1H), 7.47bs(1H) |
| c | 7.63ddd; | 6.24dd; | |
| | $J_{bc}=J_{cd}=8Hz$, $J_{ce}=2Hz$ | $J_{bc}=3Hz$, $J_{cd}=2Hz$ | |
| d | 7.15ddd; | 7.27dd; | |
| | $J_{cd}=8Hz$, $J_{de}=5Hz$, $J_{bd}=1Hz$ | $J_{cd}=2Hz$, $J_{bd}=1Hz$ | |
| e | 8.53dd; | | |
| | $J_{de}=5Hz$, $J_{ce}=1hz$ | | |

1) recorded in CDCl$_3$/D$_6$-DMSO (5/1)
2) $J_{1',2'}=3Hz$, $J_{2'a,2'b}=12Hz$
3) not identified unambiguously

| | 8a | 8b | 9[1)] |
|---|---|---|---|
| Substance No. (Proton) | R$_3$: CH$_2$— (epoxide a,b,c,O) | CH$_2$— (epoxide a,b,c,O) | a b c CH$_2$CHCH$_2$ |
| H-1 | 7.90dd | 7.90dd | |
| | | | 7.29s, 2H |
| H-2 | 7.73dd | 7.73dd | |
| H-3 | 7.34dd | 7.34dd | — |
| H-7 | 5.16m | 5.16m | 5.0–5.2m[4)] |
| H-8alpha | 2.12dd | 2.12dd | |
| | | | 2.20bs[5)] |
| H-8β | 2.25d | 2.25d | |
| H-10 | 4.92s | 4.91s | 4.81s |
| H$_2$-13 | 1.7–1.9m | 1.7–1.9m | 1.7–1.9m |
| H$_3$-14 | 1.12t | 1.12t | 1.10t |
| H-1' | 5.52t | 5.52t | 5.48m |
| H$_2$-2' | 1.7–1.9m | 1.7–1.9m | 1.5–1.7m |
| H-3' | 2) | 2) | 2.49dt |
| H-4' | 3.69bs | 3.71bs | 3.70bs |
| H-5' | 4.09q | 4.09q | 4.08q |
| H$_3$-6' | 1.40d | 1.41d | 1.37d |
| N—CH$_3$ | 2.31s | 2.35s | 2.19s |
| OH-4 | 12.16bs | 12.17bs | 6) |
| OH-6 | 12.85bs | 12.85bs | 6) |
| OH-11 | 13.64bs | 13.63bs | 6) |

TABLE 5-continued

300 MHz $^1$H NMR data of various compounds of the formula I 3)         3)         7)

1) recorded in $CDCl_3/D_6$-DMSO(5/1)
2) not identified unambiguously
3) protons a–c in the range 2.3–3.0 ppm have not been asigned unambiguously
4) overlap by $CH_2$ (c)
5) overlap by $N-CH_3$
6) phenolic OH at 12.37bs(2H) and 13.04bs(2H)
7) a: 2.99dd(1H), 3.14dd(1H); $J_{aa'}=14Hz$, $J_{ab}=J_{a'b}=6Hz$ b: 5.6–5.8m(1H) c: 5.0–5.2m (overlap by H-7)

| Substance No. (Proton) | 10<br>$R^7$: $CH_2COOCH_2CH_3$ | 12<br>$CH_2$-thienyl (a-CH$_2$, b, c, d on thiophene, S) | 13<br>$CH_2$-thienyl (a-CH$_2$, d, b, c on thiophene, S) |
|---|---|---|---|
| H-1 | 7.90dd | 7.88dd | 7.88dd |
| H-2 | 7.73t | 7.72dd | 7.72t |
| H-3 | 7.33dd | 7.33dd | 7.33dd |
| H-7 | 5.15m | 5.16m | 5.16m |
| H-8alpha | 2.11dd | 2.13dd | 2.13dd |
| H-8β | 2.26d | 2.27d | 2.27d |
| H-10 | 4.91s | 4.92s | 4.92s |
| $H_2$-13 | 1.7–1.9m | 1.7–2.0m | 1.7–2.0m |
| $H_3$-14 | 1.12t | 1.13t | 1.13t |
| H-1' | 5.51bd | 5.53bs | 5.54bs |
| $H_2$-2' | 1.7–1.9m | 1.7–2.0m | 1.7–2.0m |
| H-3' | 2.82m | 2.56m | 2.62dt |
| H-4' | 3.65bs | 3.80bs | 3.79bs |
| H-5' | 4.09q | 4.12q | 4.11q |
| $H_3$-6' | 1.40d | 1.43d | 1.43d |
| $N-CH_3$ | 2.38s | 2.12s | 2.19s |
| OH-4 | 12.16bs | 12.14bs | 12.15bs |
| OH-6 | 12.84bs | 12.84bs | 12.84bs |
| OH-11 | 13.63bs | 13.61bs | 13.62bs |
| a | 3.31d. 3.33; $J_{aa'}=19Hz$ | 3.46d. 3.66d; $J_{aa'}=14Hz$ | 3.71d. 3.83d; $J_{aa'}=14Hz$ |
| b | 4.09q | 7.02dd $J_{bc}=1Hz$, $J_{bd}=3Hz$ | 6.82dd $J_{bc}=3.5Hz$. $J_{bd}=1Hz$ |
| c | 1.16t | 6.94dd $J_{bc}=1Hz$, $J_{cd}=5Hz$ | 6.88dd $J_{bc}=3.5Hz$. $J_{cd}=5Hz$ |
| d |  | 7.24dd $J_{bd}=3Hz$, $J_{cd}=5Hz$ | 7.17dd $J_{bd}=1Hz$, $J_{cd}=5Hz$ |

| Substance No. (Proton) | 14[1)]<br>R: $CH_2$-epoxide (a, b, c, O) | 15[3)]<br>a b c<br>$CH_2CHCH_2$ |
|---|---|---|
| H-1 | 7.30s, 2H | 8.04d |
| H-2 | — | 7.79t |
| H-3 |  | 7.41d |
| H-7 | 5.13m | 5.30m |
| H-8alpha |  | 2.10dd |
| H-8β |  | 2.37d |
| H-10 | 4.83s | 4) |
| $H_2$-13 | 1.7–2.0m | — |
| $H_3$-14 | 1.10t | 2.43s |
| H-1' | 5.49bs | 5.57bd |
| $H_2$-2' | 1.7–2.0m | 1.84m |
| H-3' |  | 2.57m |
| H-4' | 3.70bs | 3.74bs |
| H-5' | 4.09q | 4.03q |
| $H_3$-6' | 1.38d | 1.38d |
| $N-CH_3$ | 2.20s | 2.23s |
| OH-4 | 2) | — |
| OH-6 | 2) | 13.31bs |
| OH-11 | 2) | 14.00bs |
| a |  | 3.0–3.25m[5)] |
| b |  | 5.7–5.9m(1H) |
| c |  | 5.13bs and 5.17d $J=3.5Hz$ |

1) recorded in $CDCl_3/D_6$-DMSO(5/1)
2) phenolic OH at 12.34bs(2H) and 12.99bs(2H)
3) $OCH_3$ at 4.10s (3H)
4) 10alpha: 2.98d; 10β: 3.23d; J=19Hz
5) overlap by H-10

TABLE 5-continued

300 MHz $^1$H NMR data of various compounds of the formula I

| Substance No. (Proton) | 16 R$^7$: CH$_2$CHCH$_2$ a b c | 17 CH$_2$CHCH$_2$ a b c | 18 CH$_2$COCH$_3$ a b |
|---|---|---|---|
| H-1 | 8.04d | 7.89dd | 7.89d |
| H-2 | 7.79t | 7.72t | 7.72t |
| H-3 | 7.39d | 7.33dd | 7.33d |
| H-7 | 5.32m | 5.15m | 5.14m |
| H-8alpha |  | 2.12dd |  |
| H-8β |  | 2.26d |  |
| H-10 |  | 4.91s | 4.91s |
| H$_2$-13 | — | 1.7–1.9m |  |
| H$_3$-14 | — | 1.12t | 1.11t |
| H-1' | 5.57bs | 5.51bs | 5.57bd |
| H$_2$-2' |  | 1.7–1.9m |  |
| H-3' |  | 2.48dt | 2.85m |
| H-4' | 3.72bs | 3.70bs | 3.86bs |
| H-5' | 4.03q | 4.08q | 4.24q |
| H$_3$-6' | 1.41 | 1.41d | 1.32d |
| N—CH$_3$ | 2.22s | 2.20s | 2.23s |
| OH-4 | — | — | 12.16bs |
| OH-6 | 13.34bs | 13.36bs | 12.84bs |
| OH-11 | 13.98bs | 13.81bs | 13.61bs |
| a |  | 2.97dd, 3.15dd; J$_{aa'}$=14Hz J$_{ab}$=J$_{a'b}$=7Hz | 2.37d, 2.57d; J$_{aa'}$=11.5Hz |
| b | 5.68–5.82m | 5.6–5.8m | 1.42s, 3H |
| c | 5.1–5.2m | 5.05–5.15m |  |
| OCH$_3$ | 4.09s | 4.09s |  |

We claim:

1. An anthracycline derivative having the formula I:

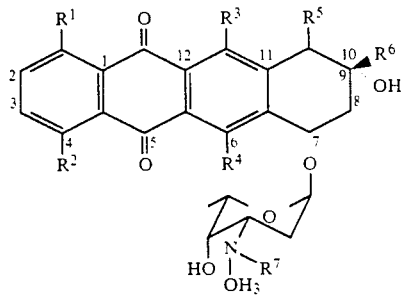

or a physiologically acceptable inorganic or organic acid addition salt thereof, wherein:
R$^1$ is hydrogen or a hydroxyl group;
R$^2$ is hydrogen, a hydroxyl or a methoxy group;
R$^3$ is hydrogen or a hydroxyl group;
R$^4$ is hydrogen or a hydroxyl group;
R$^5$ is hydrogen, a hydroxyl or a methoxycarbonyl group;
R$^6$ is CH$_2$CH$_3$, COCH$_3$COCH$_2$OH, CHOHCH$_3$ or CHOHCH$_2$OH; and
R$^7$ is an allyl radical, a propargyl radical or a glycidyl radical.

2. An anthracycline derivative as claimed in claim 1, wherein:
R$^1$ is H;
R$^2$ is H, OH or OCH$_3$;
R$^3$ and R$^4$ are OH;
R$^5$ is H; and
R$^6$ is COCH$_3$, COCH$_2$OH, CHOHCH$_3$ or CHOHCH$_2$OH.

3. An anthracycline derivative having the formula I:

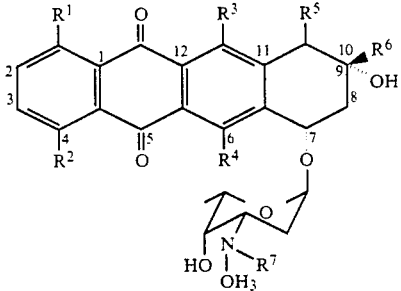

or a physiologically acceptable inorganic or organic acid addition salt thereof, wherein:
R$^1$ is hydrogen or a hydroxyl group;
R$^2$ is hydrogen, a hydroxyl or a methoxy group;
R$^3$ is hydrogen or a hydroxyl group;
R$^4$ is hydrogen or a hydroxyl group;
R$^5$ is a hydroxyl or a methoxycarbonyl group;
R$^6$ is CH$_2$CH$_3$, COCH$_3$, COCH$_2$OH, CHOHCH$_3$ or CHOHCH$_2$OH; and
R$^7$ is an allyl radical, a propargyl radical or a glycidyl radical.

4. An anthracycline derivative as claimed in claim 3, wherein:
R$^1$ is H or OH;
R$^2$, R$^3$, R$^4$, and R$^5$ are OH; and
R$^6$ is CH$_2$CH$_3$.

5. An anthracycline derivative as claimed in claim 3, wherein:
R$^1$ is H;
R$^2$ is OCH$_3$;
R$^3$, R$^4$, and R$^5$ are OH; and
R$^6$ is CH$_2$CH$_3$.

6. An anthracycline derivative as claimed in claim 3, wherein
R$^1$, R$^2$, R$^3$, and R$^4$ are OH;
R$^5$ is COOCH$_3$; and $R^6$ is $CH_2CH_3$.

7. An anthracycline derivative as claimed in claim 1, wherein $R^7$ is a glycidyl radical.

8. An anthracycline derivative as claimed in claim 3, wherein $R^7$ is a glycidyl radical.

9. An anthracycline derivative as claimed in claim 1, wherein $R^7$ is an allyl radical.

10. An anthracycline derivative as claimed in claim 3, wherein $R^7$ is an allyl radical.

* * * * *

UNITED STATES PATENT AND TRADEMARK OFFICE
CERTIFICATE OF CORRECTION

PATENT NO. : 5,260,425

DATED : NOVEMBER 9, 1993

INVENTOR(S) : PETER HERMENTIN ET AL.

It is certified that error appears in the above-identified patent and that said Letters Patent is hereby corrected as shown below:

Title page, right column, line 3 of the ABSTRACT; Column 1, lines 10-22; claim 1, column 19, lines 34-45; and in claim 3 at column 20, lines 30-42, the formula I should read:

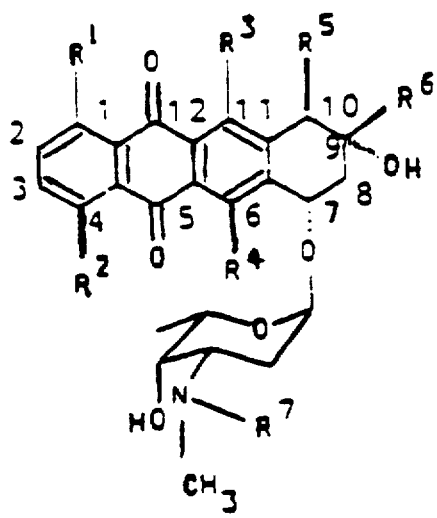

Title page, right column, line 9 of the ABSTRACT, "$R^5$ hydrogen," should read --$R^5$ is hydrogen,--.

UNITED STATES PATENT AND TRADEMARK OFFICE
CERTIFICATE OF CORRECTION

PATENT NO.    : 5,260,425
DATED         : November 9, 1993
INVENTOR(S)   : Peter Hermentin et al.

It is certified that error appears in the above-indentified patent and that said Letters Patent is hereby corrected as shown below:

In claim 1, column 19, line 55, "$COCH_3COCH_2OH$," should read --$COCH_3$, $COCH_2OH$,--.

Signed and Sealed this

Sixth Day of December, 1994

BRUCE LEHMAN

Attest:

Attesting Officer

Commissioner of Patents and Trademarks